United States Patent [19]
Karr, Jr.

[11] Patent Number: 5,657,751
[45] Date of Patent: Aug. 19, 1997

[54] CARDIOPULMONARY RESUSCITATION UNIT

[76] Inventor: Michael A. Karr, Jr., 9353 Rosstown Way, Houston, Tex. 77080-7415

[21] Appl. No.: 96,369

[22] Filed: Jul. 23, 1993

[51] Int. Cl.⁶ ........................................... A61H 31/00
[52] U.S. Cl. ........................ 128/205.18; 128/204.18; 128/204.28; 128/205.14; 128/205.13
[58] Field of Search ................ 128/200.24, 200.28, 128/204.18, 204.21, 202.13, 205.14, 205.13, 205.16, 205.18

[56] References Cited

U.S. PATENT DOCUMENTS

| | | | |
|---|---|---|---|
| 1,177,208 | 3/1916 | Pierpont | 128/202.28 |
| 1,197,232 | 9/1916 | Pierpont | 128/205.13 |
| 2,399,643 | 5/1946 | Kreiselman | 128/205.13 |
| 3,336,920 | 8/1967 | Thomas | 128/205.16 |
| 3,425,409 | 2/1969 | Isaacson et al. | 128/205.16 |
| 3,509,899 | 5/1970 | Hewson | 128/204.18 |
| 3,782,371 | 1/1974 | Derouineau | 128/205.16 |
| 3,965,893 | 6/1976 | Ragailler | 128/205.16 |
| 3,982,532 | 9/1976 | Halldin et al. | 128/206.24 |
| 4,326,507 | 4/1982 | Barkalow | 128/207.14 |
| 4,349,015 | 9/1982 | Alferness | 601/41 |
| 4,397,306 | 8/1983 | Weisfeldt | 128/205.25 |
| 4,424,806 | 1/1984 | Newman et al. | 128/205.25 |
| 4,454,881 | 6/1984 | Huber et al. | 128/207.12 |
| 4,467,799 | 8/1984 | Steinberg | 128/206.14 |
| 4,570,615 | 2/1986 | Barkalow | 128/204.21 |
| 4,898,167 | 2/1990 | Pierce et al. | 128/205.16 |
| 5,109,833 | 5/1992 | Frimberger | 128/205.13 |
| 5,313,837 | 5/1994 | Garfield et al. | 128/205.16 |
| 5,327,887 | 7/1994 | Nowakowski | 128/204.21 |

FOREIGN PATENT DOCUMENTS

| | | | |
|---|---|---|---|
| 4038499 | 6/1992 | Germany | 128/200.24 |
| 21987793 | 6/1988 | United Kingdom | 128/205.16 |
| 911567 | 10/1991 | WIPO | 128/200.28 |

*Primary Examiner*—Edgar S. Burr
*Assistant Examiner*—William J. Deane, Jr.

[57] ABSTRACT

A method and apparatus for providing cardiopulmonary resuscitation, CPR, are disclosed. A manually operated air pump is positioned on the patient's chest. A mask is positioned on the patient's face. An air line connects the mask to the air pump. Vertically downward stokes are applied to the air pump. The downward strokes provide resuscitative chest compressions and charge an air holding tank. Periodically, the contents of the air holding tank are discharged through the air line and into the mask to provide resuscitative patient ventilations. In one embodiment, the compressions are provided in response to signals from a timing device and the ventilations are provided automatically.

19 Claims, 3 Drawing Sheets

CARDIOPULMONARY RESUSCITATION UNIT

BACKGROUND OF THE INVENTION

In one aspect, this invention relates to a method of providing cardiopulmonary resuscitation. In another aspect, this invention relates to a device for providing cardiopulmonary resuscitation.

Medical emergencies happen all the time, and many lives are saved because a paramedic or passerby can perform cardiopulmonary resuscitation (CPR) and keep the victim breathing and maintain blood circulation until proper medical attention is available. Yet many people are unprepared to provide CPR should the situation arise. Even those who have been properly trained often do not use their training frequently enough to make it easy for them to recall exactly what to do under the pressure of an emergency situation. A simple way to administer CPR would be very desirable.

As an additional factor, many people find the very idea of kissing a corpse to administer CPR to be repugnant. Further, CPR must sometimes be administered under revulsive conditions, such as in the presence of body fluids and/or offensive aromas. Also, the patient may vomit during the administration of CPR. These factors can induce an intense desire in the person administering the CPR to stop. Also, many people are concerned about contracting infectious diseases such as AIDS, tuberculosis, or Hepatitis B by administering CPR, especially to strangers. A technique to administer CPR without requiring intimate contact by the rescuer would be very desirable.

An additional problem is that administering CPR can be physically exhausting. The rescuer must both make the required chest compressions and the required breath cycles many times each minute and may have to continue for an extended period of time. Considerable force must be applied on the chest compressions. Considerable force must also be exerted in order to inflate the patient's chest. Often the rescuer will already be physically exhausted from the ordeal of moving the victim to a place where CPR can be administered or the rescuer will be elderly and not in prime physical condition. A technique for applying CPR that is less physically demanding would be very desirable.

A rescuer's sense of time is often distorted in an emergency situation. It is important during the administration of CPR to perform the compressions and inflations sufficiently rapid to preserve the patient, but not with such rapidity to prematurely exhaust the rescuer. A CPR device to facilitate providing properly timed chest compressions and provide an automatic supply of breathing air timed to the chest compressions would be very desirable.

OBJECTS OF THE INVENTION

It is an object of this invention to provide a CPR device that is simple and easy to use.

It is another object of this invention to provide a CPR device that eliminates the need for close physical contact with the patient.

It is a further object of this invention to provide a CPR device that offers less tiring operation, and can be actuated by arm or leg operation, for example.

It is yet another object of this invention to provide a CPR device that is compact and inexpensive, and that partially automates part of the process of providing CPR to a patient.

SUMMARY OF THE INVENTION

In one embodiment of the invention, there is provided a method for providing cardiopulmonary resuscitation, CPR. The patient should be lying on his/her back. A manually operated air pump is positioned on the patient's chest. A mask is positioned on the patient's face. An air line connects the mask to the air pump. Vertically downward strokes are applied to air pump. The downward strokes should be of sufficient force to provide resuscitative chest compressions and to charge an air holding tank. Periodically, the contents of the air holding tank are discharged through the air line and into the mask to provide resuscitative patient ventilations. Preferably, in the range of 40 to 80 chest compressions and in the range of 5 to 15 patient chest ventilations should be provided per minute. In a preferred embodiment, the compression strokes are provided in response to visual signals from a timing device and the ventilations are provided automatically.

In another embodiment of the invention, an apparatus is provided for carrying out the above process. The apparatus includes a means for defining a reciprocating-wall pumping chamber. To draw air into the pumping chamber, there is provided a means for establishing a first flow path from the atmosphere into the pumping chamber. To prevent air flow back out of the pumping chamber during the downward stroke, there is provided a first one-way valve means positioned in the first flow path means. The pumping chamber empties into a means for defining a holding chamber via means for establishing a second flow path from the pumping chamber into the holding chamber. To prevent air flow back out of the holding chamber during the upward stroke, a second one-way valve means is positioned in the flow second path means. A valve means is positioned in flow communication with the holding chamber for selectively discharging the contents of the holding chamber in response to a counter. A counter is provided to actuate the valve means. Preferably, the selective discharge valve is actuated in response to the passage of a predetermined number of cycles of the means for defining the pumping chamber.

Preferably, the CPR device is made of inexpensive material such as plastic and is compactly sized. It is further preferred that the device be provided in kit form together with an air hose and a soft mask to provide air to the patient, as well as with a timing device to indicate when compression strokes should be administered. The preferred kit thus provides a partially automated way of administering CPR, providing an indicator for properly timed chest compressions in combination with automatically timed breathing.

These embodiments of the invention eliminate the need for direct physical contact with the patient, thereby reducing the possibility of infections being passed. The physical strain of administering CPR is reduced because the CPR device partially automates the CPR process. When the device is designed with a low center of gravity, it can be operated by foot for long periods of time without physical exhaustion.

DETAILED DESCRIPTION OF THE PREFERRED EMBODIMENTS

In accordance with one embodiment of the invention, there is provided a method for providing a patient or victim with cardiopulmonary resuscitation (CPR). If not already positioned on his/her back, the patient should be placed on their back. A manually operated air pump is placed on the patient's chest. The patient's mouth and nose are then covered by a mask and the mask is connected by an air line to the air pump. The air pump is usually connected to the mask via an air holding tank which is also positioned on the patient's chest. The air holding tank is charged by using vertically downward strokes on the manually operated air pump. The vertically downward strokes provide resuscitative chest compressions, while the air tank is charged. Periodically, the contents of the air holding tank are discharged through the air line and into the mask thereby providing resuscitative patient ventilation. The method is preferably carded out so as to provide in the range of 40 to 80 chest compressions per minute and in the range of 5 to 15 patient ventilations per minute.

In a preferred embodiment of the invention, the CPR unit comes in protective packaging. When the packaging is removed, an electronic cadence device is automatically actuated. The cadence device emits cadence signals and the vertically downward strokes on the air pump are provided responsively to the cadence signals thereby assuring an optimal rate of chest compression. By coupling the discharge of the contents of the air holding tank to either the chest compressions or the passage of time, adequate rate of patient ventilation can be maintained.

Figure 4:
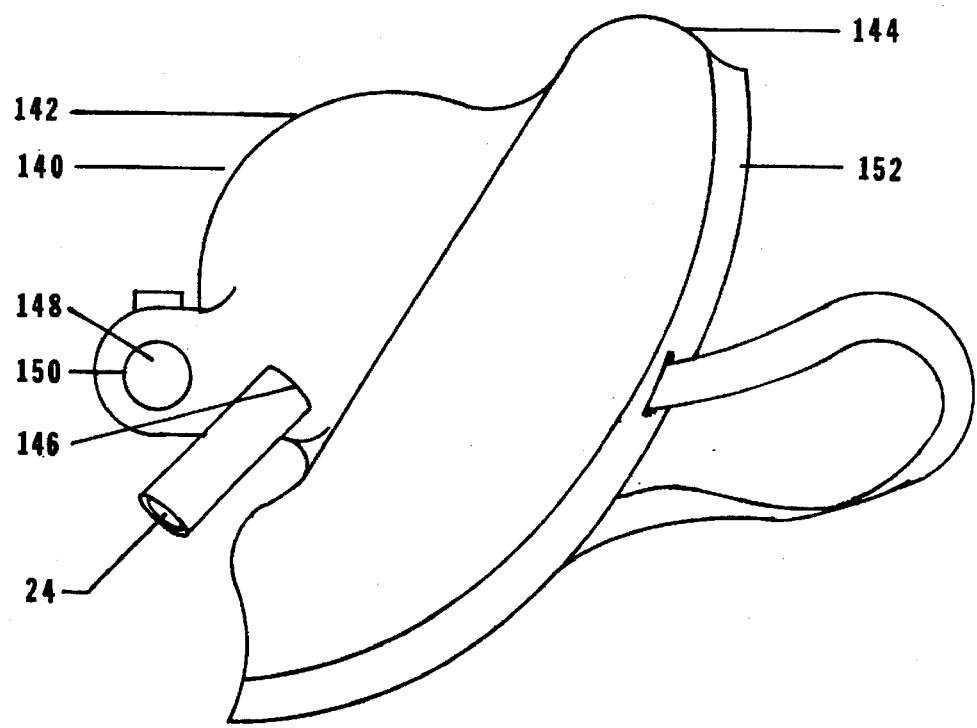
FIG. 4 is a pictorial representation of a device embodying certain additional features of the invention.
Figure 5:
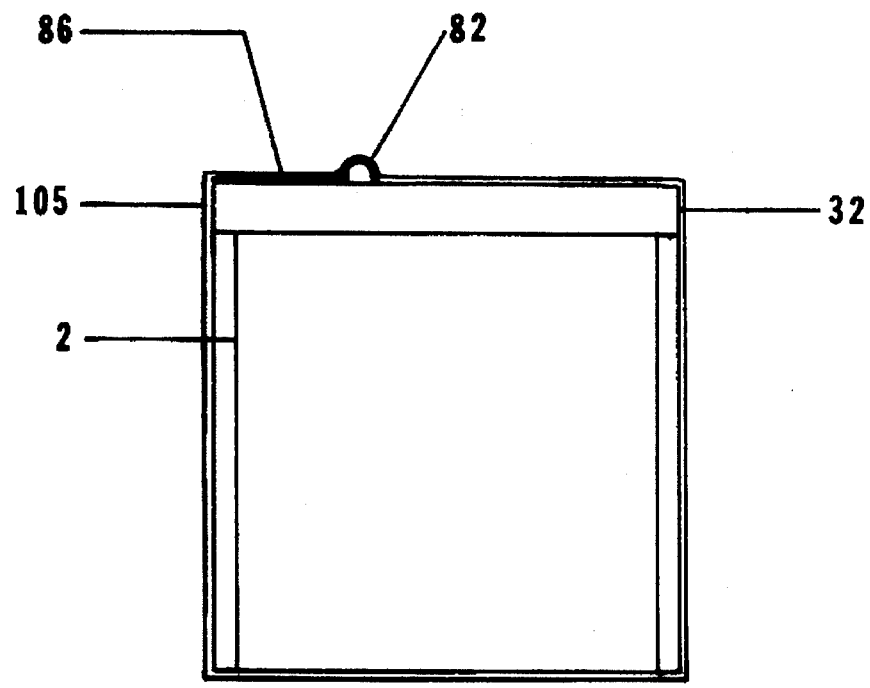
FIG. 5 is a representational schematic arrangement drawing of the CPR device as packaged.
Figure 6:
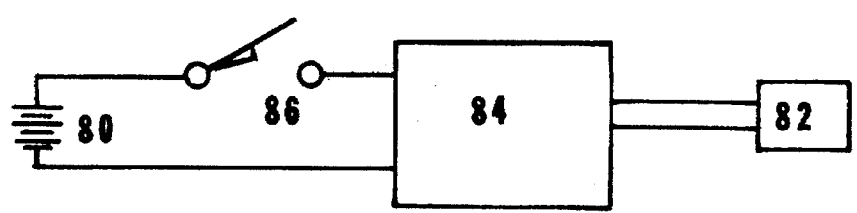
FIG. 6 is a circuit schematic of the power source, switch, timing device and LED of the present invention.

In accordance with the embodiment of the invention shown in the figures, an apparatus 2 is provided with a means 4 for defining a reciprocating-wall pumping chamber 6. A first means 8 establishes a first flow path from the atmosphere into the pumping chamber 6. Means 14 defines a holding chamber 12. A second means 10 establishes a second flow path from the pumping chamber 6 to the holding chamber 12. A one way valve means 16, such as a flapper valve or check valve is positioned in the means forming the first flow passage 8 to prevent backflow from the pumping chamber 6 to the atmosphere. At least one one-way valve means 18 is positioned in second means 10 forming the second flow path to prevent backflow from the holding chamber 12 to the pumping chamber 6. A valve means 20 is positioned in flow communication with the holding chamber 12 for selectively discharging the contents of the holding chamber. A counter 22 is provided to actuate the valve means 20. The counter 22 can be either mechanical or electrical. However, a mechanical counter is preferred. The valve means 20 is in flow communication with an air line or tubing, schematically represented by arrow 24 which is connected to a mask (see FIG. 4).

Figure 1:
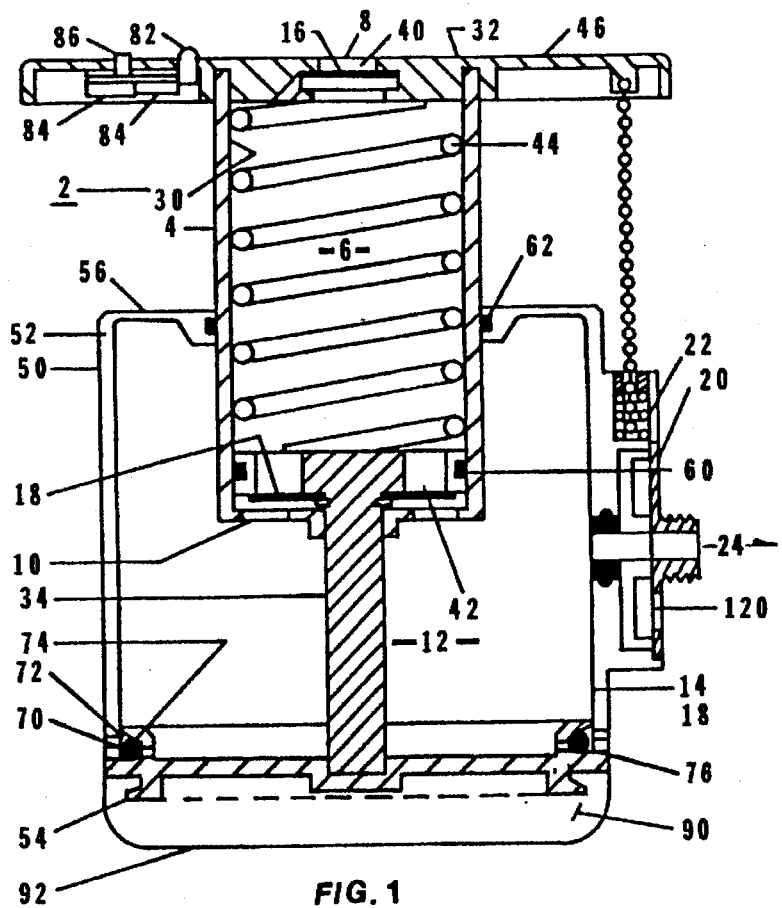
FIG. 1 is a side sectional view of one embodiment of present invention.
Figure 2:
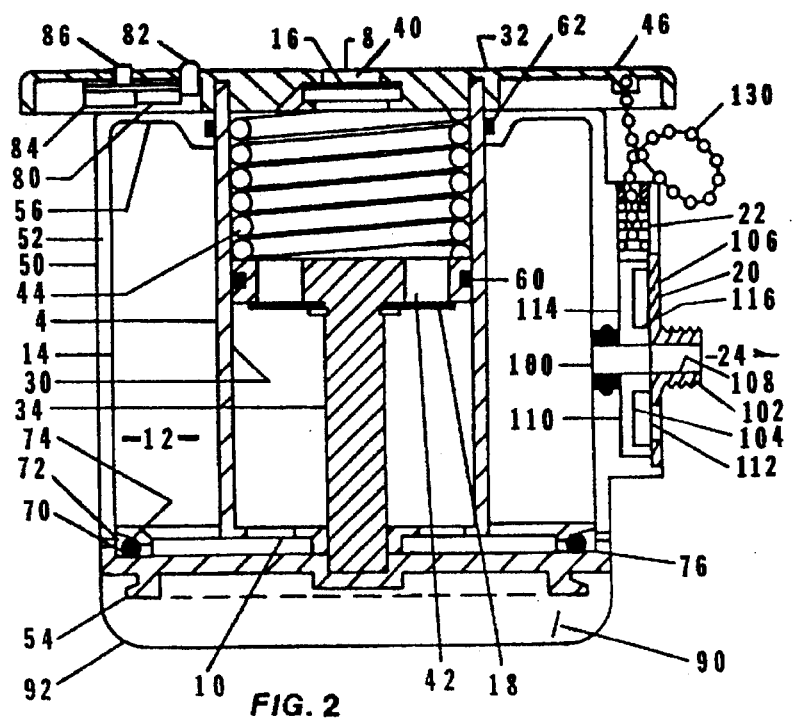
FIG. 2 is a side sectional view of the embodiment of the invention shown in FIG. 1 in another portion of the operation cycle.

The method of the invention can be carried out with many types of reciprocating wall pumping chambers. For example, a bellows can be used. Where the apparatus is to be constructed with hard plastic or metal, the pumping chamber 4 will generally be defined by a cylinder 30, end closure 32 closing the end of the cylinder 30, and a piston 34 closely slidably received by the cylinder 30. Such reciprocating wall pumping wall chambers can be constructed with either or both of the cylinder and piston reciprocally movable with respect to the other. Generally speaking, the movement will be from the first position in which the piston and the end closure are spaced apart as illustrated in FIG. 1 to the second position in which the piston and end closure are spaced apart a lesser distance as shown in FIG. 2. A pumping cycle is constituted by movement of the piston and cylinder from the first position to the second position and then back again.

In the illustrated embodiment of the invention, the piston 34 is fixedly mounted with respect to the means for defining the holding chamber. The cylinder 30 is slidably mounted with respect to the piston 34 and the means 14 defining the holding chamber. The first flow path 8 includes a passage 40 extending through the enclosure 32 of the cylinder. The second flow path 10 includes a passage 42 extending through the piston 34. A spring 44 is provided to bias the end closure 32 away from the piston 34. In the illustrated embodiment, the spring 44 is positioned inside of the chamber 6. A handle 46 is attached to the end closure 32. In the illustrated embodiment, the handle 46 attaches to the periphery of the end closure 32 forming a lid or rim-type structure which can be gasped with both hands if desired, or foot actuated.

It is desirable that the CPR device of the invention be stable when positioned on a patient's chest. Therefore, it is preferred that the device have a large width with respect to its height so that it will be stable when placed on a patient. It could also be provided with a strap (not shown) if desired.

Typically, the CPR device will have a volume in the range of 1 to 3 liters. The means 14 defining the holding chamber in the preferred embodiment is formed by a housing 50 having a sidewall 52, preferably of a generally cylindrical or tubular configuration. A bottom end closure 54 is mounted to a lower end of the sidewall 52. An upper end closure, preferably generally annular in shape, is mounted to an upper end of the sidewall 52. The upper end closure 56 has a passage extending through it and the cylinder 30 is preferably slidably mounted in the passage. The piston 34 is preferably fixedly mounted to the bottom end closure 54 of the housing. The valves 16 and 18 in a preferred embodiment of the invention are check valves or flapper valves. These valves are generally formed from an elastomeric or other substance to effect closure of the air ports. A ring seal means 60 formed from rubber, for example, is mounted peripherally to the piston 34 between the piston 34 and the cylinder wall 30. A ring seal means 62 is mounted on the inside periphery of the passage through the upper end closure 56 of the housing 50 between the upper end closure 56 and the cylinder 30.

In a further embodiment of the invention a valve means 70 is provided to prevent overpressurization of the holding chamber 12. The valve means 70 is generally formed by a passage 72 extending through the sidewall 52 of the housing 50 and a pressure release valve means 74 which seals the passage. Generally speaking, the pressure release valve means is biased to seal the passage until a predetermined pressure difference across the passage is exceeded. One such suitable valve means is illustrated in the Figures and is formed by an O-ring type seal seated on the passage 72. The O-ring seal is seated in a groove 76 which extends circumferentially around the sidewall 52 of the housing 50 and the flowpath 72 opens into the bottom of the groove.

In a further preferred embodiment of the invention, the CPR device includes a battery 80 an indicator such as light emitting diode (LED) 82 and a timer 84. Preferably, the timer 84 is formed by a circuit board such as a solid state timing circuit board. The battery 80 can be a component in the circuit board if desired. The battery 80, timer 84 and LED 82 are electrically connected by suitable means. The LED 82 is preferably positioned on the upper end surface of the apparatus so that it can be readily viewed by the operator. The timer 84 actuates the LED flasher to flash at a frequency in the range of 40 to 80 times per minute. The user of the apparatus can then perform compression strokes at a cadence indicated by the flasher to provide the patient with chest compressions at a sufficient rate for good results. The battery and solid state timing circuit are mounted by any suitable means so as to be in operable association with LED flasher. For convenience, they can be mounted in the handle 46 as illustrated.

In a preferred embodiment of the invention, a resilient pad 90 is mounted to a lower end surface of the bottom end closure 54 of the housing. The pad 90 can be retained by any suitable means to the housing. In a preferred embodiment, the pad has an upper end surface which is mounted to a lower end surface of the housing. The pad 90 has a lower end surface 92 which is preferably molded to conform to an area defined by the intersection of a patient's rib cage and their sternum. The resilient pad can be formed by any suitable material. For example, foam rubber can be used. A major portion of the pad should rest on a lower portion of the patient's sternum for optimal location.

In a preferred embodiment of the invention, the pumping chamber 6 will generally have a volume in the range from about 200 to 400 cubic centimeters. The holding chamber will generally have a volume in the range of from about 800 up to about 3000 cubic centimeters. Lung capacity of an adult ranges from about 4 to about 6 liters. At rest however, only about 0.4 liters is normally inspired or exhaled although deep breathing can result in the displacement of about 3 to 4 liters. It is believed that a holding chamber 12 sized to provide from about 600 up to about 1600 cc's will provide good results while minimizing the risk of injuring small adults or children. The cross sectional area of the pumping chamber 6 should be sized to provide a minimum of 20 pounds of resistance as the holding chamber comes to pressure. The effort required to pump the device can be varied by selection of the cross sectional area of the cylinder 30 as well as by the strength of the spring 44. Generally speaking, the relative volume of the chambers 6 and 12 will range from 1:3 to 1:12, such as in the range of 1:4 or 1:8. Usually, the holding chamber will discharge every 4 to 8 cycles of the pumping chamber. In a preferred embodiment of the invention, the LED 82 is actuated by a switch 86 also positioned on the upper end surface of the device. Preferably, the CPR device 2 is packaged and stored in a protective packaging, with the switch 86 retained in the depressed position by an encircling band or tape or the like. The packaging is attached to the band or tape so that the switch will be actuated by being released to the upright position when the packaging is removed thereby completing the circuit with a battery and the actuating the electronic cadence device.

In a preferred embodiment of the invention, the valve means 20 for selectively discharging the contents of the holding chamber 12 includes a discharge port 100 forming a flow path through the means 14 defining the holding chamber. In this embodiment, the apparatus generally further comprises a nozzle 102 positioned at a spaced apart distance from the discharge port 100. A valve body 104 is mounted between the discharge port 100 and the nozzle 102. The valve body 104 is movable from a first position in which no flow path is formed between the discharge port 100 and the nozzle 102 to a second position in which a flow path is formed between the discharge port and the nozzle. In the illustrated embodiments, the valve body 104 is in the second position.

Figure 3:
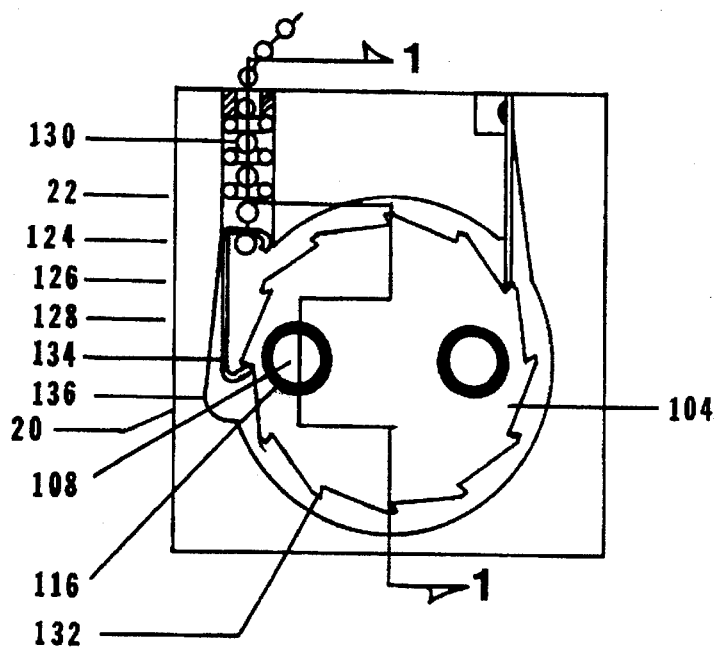
FIG. 3 is a pictorial representation of a portion of the device as shown in FIGS. 1 and 2 with a cover removed to show internal details.

In the illustrated embodiments, the nozzle 102 is positioned on a cover 106 which has been removed from the view of the valve means as shown in FIG. 3. It should also be noted that the relationship between FIG. 3 and FIG. 1 is illustrated by cut lines 1—1 in FIG. 3 which do not form a straight line. A variety of valves capable of incremental movement to reach a discharge position can be used to practice the preferred embodiments of the invention. The valve body 104 in the illustrated embodiment of the invention is generally disk shaped and has a longitudinal axis about which the valve body rotates. The flow passage 108 extends generally longitudinally through the valve body 104 at a spaced apart distance from the longitudinal axis. Generally speaking, the valve body 104 has an intake side 110 facing the holding chamber 12 and an exhaust side 112 facing the nozzle 102. The valve body has a seal surface 114 on the intake side 110 to seal the discharge port 100 when the passage through the valve body is out of alignment with the discharge port and a nipple 116 on the discharge side positioned peripherally around the passage 108 to seal with the nozzle 102 when the nipple is aligned with the nozzle. When the nipple is out of alignment with the nozzle, backflow from the line 24 is permitted and can be exhausted via a port 120. This provides an exhalation path for the patient. Generally speaking, the valve means 20 is actuated by a counter 22. In the illustrated embodiment, the counter 22 is mechanical in nature. Generally speaking, the means 22 is formed by a means 124 cooperating with the pumping chamber and with valve body 104 for incrementally moving the valve body 104 in response to pumping cycles of the pumping chamber 6. In one embodiment of the invention, the means 124 includes a means 126 for clutching the valve body 104. A mounting means 128 such as a recess in the housing is provided for mounting the clutch means 126 adjacent to the valve body 104. A linkage 130 attaches the means defining pumping chamber with the clutch means 126. In the illustrated embodiment, the means for clutching the valve body is provided by rachet teeth 132 positioned on a generally cylindrical periphery of the valve body 104 in combination with an actuating pawl 134 which is retained in position in the housing by recess 136 and cover 106.

In a preferred embodiment of the invention, the apparatus further comprises a face mask 140 connected to the CPR device to by tubing 24. The face mask 140 has a rigid central portion 142 and a flexible peripheral portion 144. The mask has an inner surface and an outer surface. The rigid central portion 142 has a first passage 146 extending through it. The tubing 24 is connected to the passage 146. In a preferred embodiment, the mask 140 further has a second passage 148 extending through the rigid portion 142. The passage 148 carries a priority valve 150 which permits the patient to breathe freely once recovery is underway. In a further preferred embodiment of the invention, a strip of adhesive material 152 is positioned on the outer periphery of the inner surface of the flexible portion of the mask. The adhesive material permits a good seal to be maintained between the mask and the patient's face as well as providing a means so that the mask can be folded or pinched in order to accommodate a range of face sizes.

While certain embodiments of the invention have been described herein, the invention is not to be construed as so limited except to the extent such limitations are found in the claims.

I claim:

1. Apparatus comprising:
   a. a manually operated pump means having a reciprocating wall pumping chamber, said reciprocating wall pumping chamber comprising:

i. a cylinder;

ii. an end closure on said cylinder; and iii. a piston closely slidably received in the cylinder, b. means establishing a first flow path from the atmosphere into the pumping chamber;

c. first one-way valve means in the first flow path means to prevent backflow from the pumping chamber to the atmosphere;

d. a holding chamber, said holding chamber comprising:
a housing having a sidewall;
a bottom end closure mounted to a lower end of the side wall; and
an upper end closure mounted to an upper end of the sidewall, wherein the upper end closure has a passage therethrough and the cylinder is slidably mounted in the passage; and wherein the piston is fixedly mounted to the bottom end closure of the housing;

e. means establishing a second flow path from the pumping chamber into the holding chamber;

f. a second one-way valve means in the second flow path means to prevent backflow from the holding chamber to the pumping chamber;

g. valve means in flow communication with the holding chamber for selectively discharging the contents of the holding chamber; and h. counter means coupled to the selective discharge valve means for actuating said valve means in response to a determined number of actuations of said pump means, wherein at least one of said piston and cylinder being adapted for reciprocating movement with respect to the other from a first position in which the piston and the end closure are spaced apart a first distance to a second position in which the piston and the end closure are spaced apart a second distance which is less than the first distance and back again to the first position, wherein the movement from the first position to the second position and back again constitutes a pumping cycle.

2. The apparatus as in claim 1 in combination with a protective packaging means for said apparatus, said apparatus including a switch retained in a depressed position by an encircling band, a battery, a circuit, an electronic cadence device, said protective packaging being attached to said band, such that said switch is released from the depressed position to an upright position, responsive to removal of said apparatus from said protective packaging, thereby completing said circuit with said battery and actuating said electronic cadence device.

3. Apparatus comprising:

a. a means for defining a reciprocating-wall pumping chamber;

b. a means for establishing a first flow path from the atmosphere into the pumping chamber:

c. a first one-way valve means positioned in the first flow path means to prevent backflow from the pumping chamber to the atmosphere;

d. means for defining a holding chamber;

e. means for establishing a second flow path from the pumping chamber into the holding chamber;

f. a second one-way valve means positioned in the second flow path means to prevent backflow from the holding chamber to the pumping chamber;

g. a valve means positioned in flow communication with the holding chamber for selectively discharging the contents of the holding chamber, said valve means for selectively discharging the contents of the holding chamber including a discharge port forming a third flow path through the means defining the holding chamber; and h. a counter means coupled to the selective discharge valve means for actuating said valve means;

said apparatus further comprising:

i. a nozzle positioned spaced apart a distance from the discharge port, and ii. a valve body having at least one passage therethrough and mounted between the discharge port and the nozzle, said valve body being moveable from a first position in which no flow path is formed between the discharge port and the nozzle to a second position in which a flow path is formed between the discharge port and the nozzle.

4. The apparatus as in claim 3 in combination with a protective packaging means for said apparatus, said apparatus including a switch retained in a depressed position by an encircling band, a battery, a circuit, an electronic cadence device, said protective packaging being attached to said band, such that said switch is released from the depressed position to an upright position, responsive to removal of said apparatus from said protective packaging, thereby completing said circuit with said battery and actuating said electronic cadence device.

5. Apparatus as in claim 3 wherein said valve body is generally disk-shaped and has a longitudinal axis and said at least one passage extends generally longitudinally through the valve body spaced from said longitudinal axis, said disk-shaped valve body being movable from a first position in which each said at least one passage is out of alignment with the discharge port to a second position in which at least one of said at least one passages is in alignment with the discharge port.

6. Apparatus as in claim 3 further comprising:

means cooperating with the pumping chamber and with the valve body for incrementally moving the valve body in response to pumping cycles of the pump means.

7. Apparatus as in claim 5 wherein the valve body has an intake side facing the holding chamber and an exhaust side facing the nozzle, said valve body having a seal surface on the intake side to seal the discharge port when each said at least one passage through the valve body is out of alignment with the discharge port and a nipple on the discharge side positioned peripherally around the passage to seal with the nozzle when the nipple is aligned with the nozzle and to permit backflow through the nozzle when the nipple is out of alignment with the nozzle.

8. Apparatus as in claim 7 wherein the means cooperating with the pumping chamber and the valve body for incrementally advancing the valve body in response to the pumping cycles of the pump means comprises:

i. clutch means;

ii. means mounting said clutch means adjacent to the valve body; and iii. linkage means attaching the pumping chamber with the clutch means.

9. Apparatus as in 1 wherein the piston is fixedly mounted with respect to the holding chamber; the cylinder is slidably mounted with respect to the piston and to the holding chamber; the first flow path includes a passage extending through the end closure of the cylinder; and the second flow path includes a passage extending through the piston;

said apparatus further comprising:
spring means mounted to urge the end closure away from the piston and bias the pumping chamber toward the first position; and
a handle attached to the end closure, the handle and end closure together forming an upper end surface of the apparatus.

10. Apparatus as in claim 9 wherein the holding chamber comprises:
a housing having a sidewall;
a bottom end closure mounted to a lower end of the sidewall; and
an upper end closure mounted to an upper end of the sidewall, wherein the upper end closure has a passage therethrough and the cylinder is slidably mounted in the passage; and
wherein the piston is fixedly mounted to the bottom end closure of the housing.

11. Apparatus as in claim 10 wherein the first one-way valve means is formed by a first check valve in the passage through the end closure on the cylinder; and the second one-way valve means is formed by a second check valve in the passage through the piston;
said apparatus further comprising:
a first ring seal means mounted peripherally to the piston between the piston and the cylinder;
a second ring seal means mounted on the inside periphery of the passage through the upper end closure of the housing between the upper end closure and the cylinder;
means establishing a fourth flow path between the holding chamber and the atmosphere, said fourth flow path means including a passage extending through the sidewall of the housing; and
a pressure relief valve means sealing said passage extending through the sidewall of the housing, said pressure relief valve means being biased to seal said passage until a predetermined pressure difference across said passage is exceeded.

12. Apparatus as in claim 11 wherein the pressure relief valve is formed by a groove extending circumferentially around the sidewall of the housing and a resilient ring seated in said groove, wherein the fourth flow path opens into the bottom of the groove.

13. Apparatus as in claim 10 further comprising:
cadence indicating means having
i. a battery;
ii. light emitting diode flasher positioned on the upper end surface of the apparatus;
iii. means electrically connecting the battery with the L.E.D. flasher;
iv. a timing circuit to actuate the L.E.D. to flash at a frequency in the range of 40 to 80 times per minute;
v. means electrically connecting the timing circuit with the flasher and with the battery; and
vi. means mounting the battery and the timing circuit in operable association with the L.E.D. flasher.

14. Apparatus as in claim 10 further comprising:
a resilient pad mounted to a lower end surface of the bottom end closure of the housing, said pad having a lower end surface molded to conform to an area defined by the intersection of a patient's rib cage and sternum.

15. Apparatus as in claim 1 further comprising:
a face mask; and
tubing connecting the face mask with the valve means for selectively discharging the contents of the holding chamber.

16. Apparatus as in claim 15 wherein the face mask comprises a rigid central portion and a flexible peripheral portion, said mask having an inner surface and an outer surface, said rigid central portion having a first passage therethrough and a second passage therethrough, the tubing being connected to the first passage.

17. Apparatus as in claim 16 further comprising:
a strip of adhesive material positioned on the outer periphery of the inner surface of the flexible portion of the mask.

18. Apparatus as in claim 16 further comprising:
a priority valve means positioned in the second passage, said priority valve means permitting a patient to breathe freely.

19. Apparatus as in claim 1 wherein the pumping chamber has a volume in the range of about 200 to about 400 cubic centimeters and the holding chamber discharges every 4 to 8 cycles of the pump means and the holding chamber is generally cylindrically shaped and has a volume in the range of 800 to 3000 cubic centimeters.

* * * * *